US010675484B2

(12) United States Patent
Li et al.

(10) Patent No.: US 10,675,484 B2
(45) Date of Patent: Jun. 9, 2020

(54) IMAGING METHOD USING RADIATION SOURCE, SHIELDING BODY, TREATMENT HEAD, AND TREATMENT DEVICE

(71) Applicant: OUR NEW MEDICAL TECHNOLOGIES, Guangdong (CN)

(72) Inventors: Jinsheng Li, Huntingdon Valley, PA (US); Haifeng Liu, Guangdong (CN)

(73) Assignee: OUR NEW MEDICAL TECHNOLOGIES, Guangdong (CN)

( * ) Notice: Subject to any disclaimer, the term of this patent is extended or adjusted under 35 U.S.C. 154(b) by 0 days.

(21) Appl. No.: 16/310,598

(22) PCT Filed: Jun. 23, 2016

(86) PCT No.: PCT/CN2016/086836
§ 371 (c)(1),
(2) Date: Dec. 17, 2018

(87) PCT Pub. No.: WO2017/219308
PCT Pub. Date: Dec. 28, 2017

(65) Prior Publication Data
US 2019/0336794 A1 Nov. 7, 2019

(51) Int. Cl.
*A61N 5/10* (2006.01)
(52) U.S. Cl.
CPC ......... *A61N 5/1039* (2013.01); *A61N 5/1001* (2013.01); *A61N 5/1031* (2013.01);
(Continued)
(58) Field of Classification Search
CPC .. A61N 5/1039; A61N 5/1048; A61N 5/1031; A61N 5/1001; A61N 2005/1094;
(Continued)

(56) References Cited

U.S. PATENT DOCUMENTS

2009/0099559 A1 4/2009 Dhadwal
2009/0161818 A1* 6/2009 Sakurai ............... A61N 5/1048
378/15

FOREIGN PATENT DOCUMENTS

CN 101797161 A 8/2010
CN 102256434 A 11/2011
(Continued)

OTHER PUBLICATIONS

International Search Report of PCT/CN2016/086836 dated Mar. 20, 2017.

*Primary Examiner* — Kiho Kim
(74) *Attorney, Agent, or Firm* — Daniel J. Chalker; Edwin S. Flores; Chalker Flores, LLP (57) ABSTRACT

An imaging method uses a radiation source, shielding body, therapeutic head, and treatment device. The imaging method uses the radiation source is applied in the treatment device. The treatment device includes a radiation source. The imaging method comprises: the radiation source emitting a radiation beam having a first energy; primary scattering the radiation beam emitted by the radiation source to emit a radiation beam having a second energy; the radiation beam after primary scattering passing through a human body lesion, wherein the second energy is lower than the first energy; receiving the radiation beam passing through the human body lesion; and establishing a lesion image according to the received radiation beam.

20 Claims, 6 Drawing Sheets

(52) U.S. Cl.
CPC .... *A61N 5/1048* (2013.01); *A61N 2005/1019* (2013.01); *A61N 2005/1094* (2013.01)

(58) Field of Classification Search
CPC .... A61N 2005/1019; A61N 2005/1054; A61B 6/00; A61B 6/0457; A61B 6/06; A61B 6/483; A61B 6/4035; A61B 6/482; A61B 5/107; A61B 5/1049
See application file for complete search history.

(56) References Cited

FOREIGN PATENT DOCUMENTS

| | | |
|---|---|---|
| CN | 202036230 U | 11/2011 |
| CN | 102844076 A | 12/2012 |
| CN | 103106940 A | 5/2013 |
| CN | 104118679 A | 12/2014 |
| CN | 105396229 A | 3/2016 |
| CN | 105641814 A | 6/2016 |

\* cited by examiner

IMAGING METHOD USING RADIATION SOURCE, SHIELDING BODY, TREATMENT HEAD, AND TREATMENT DEVICE

TECHNICAL FIELD

The present disclosure relates to the field of a medical equipment technology, and in particular to an imaging method using a radiation source, a shielding body, a therapeutic head and a treatment device.

BACKGROUND

In radiation therapy, the radioactive rays are emitted from a radiation source, and then focused on the same focus target, so that the focus target corresponds to the position of a lesion of a human body or other lesions, and the lesion is killed through the radioactive rays, thereby achieving a noninvasive treatment.

Figure 1:
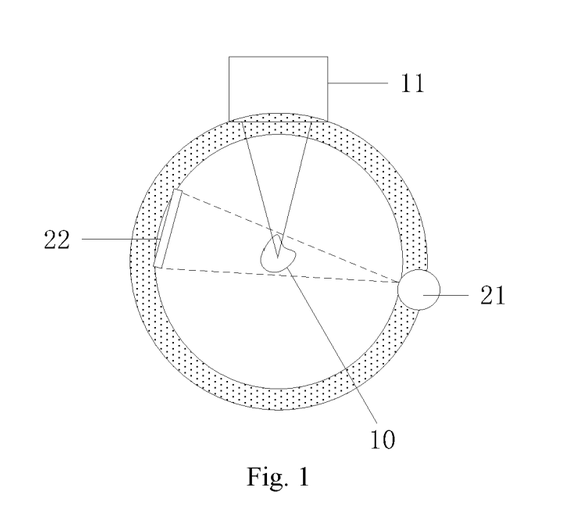
FIG. 1 is a schematic diagram of an existing treatment device.

The core components in the existing treatment device, as shown in FIG. 1, include a therapeutic head 11 and an image guiding device. The image guiding device includes a bulb tube 21 and a first detector 22 corresponding to the bulb tube 21. The therapeutic head 11 emits the radioactive rays having a treatment level energy for irradiation on a lesion 10. The bulb tube 21 is configured to emit x-rays, which are received by the first detector 22 after passing through the lesion 10 of a patient. The first detector 22 acquires lesion data according to the received x-rays passing through the lesion 10 of the human body, and performs imaging on the lesion 10 of the human body, to perform pre-treatment positioning and lesion tracking during the treatment, so that the lesion 10 receives a specific dose of beam irradiation at a target location.

Figure 2:
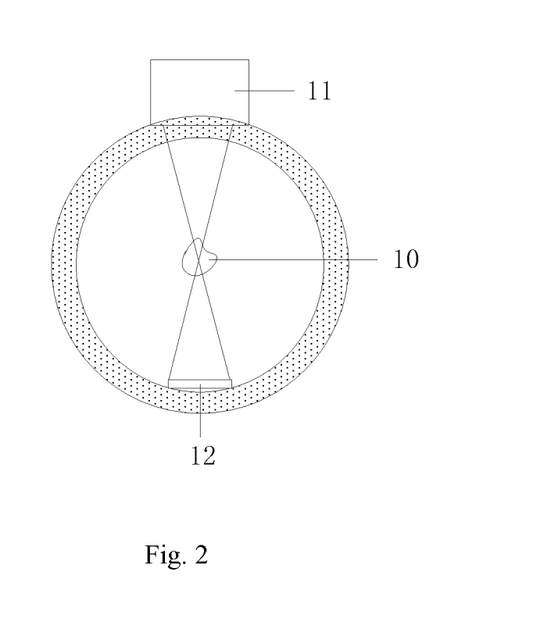
FIG. 2 is a schematic diagram of another existing treatment device.

On the one hand, the therapeutic head of the existing treatment device is relatively large, leading to a small space for a treatment chamber, while the image guiding device further compresses the treatment space, and increases the system complexity. On the other hand, the image guiding device is expensive, and the use of multiple detectors increases the device cost. Accordingly, some manufacturers utilize a treatment beam of the therapeutic head for imaging, i.e., as shown in FIG. 2, the treatment device includes the therapeutic head 11 and a second detector 12 corresponding to the therapeutic head 11. The radioactive rays having treatment level energy emitted by the therapeutic head 11 are received by the second detector 12 after passing through the lesion 10 of the human body, so as to image the lesion 10 of the human body.

Although the cost can be reduced in this way, the beam of rays having the treatment level energy emitted by the therapeutic head has a relatively high energy and a strong penetrability, so that the intensity attenuation in different substances is not much different, so that the contrast of the images directly formed by the treatment beam is relatively poor. Besides, in the pre-treatment positioning by using the beam of rays having the treatment level energy, the patient will receive a large amount of additional radiation dose, which may cause secondary tumors and other lesions and is not conducive to the health of the patient.

SUMMARY

There are provided in embodiments of the present disclosure an imaging method using a radiation source, a shielding body, a therapeutic head and a treatment device. The imaging method can scatter the high-energy beam of rays emitted by the radiation source, so as to reduce the energy of the beam of rays. The low-energy beam of rays is used for imaging of the lesion. Therefore, not only the contrast of the lesion imaging is improved, but also the additional radiation received by the patient is reduced.

In order to achieve the above objective, the embodiments of the present disclosure adopt technical solutions as follows.

In one aspect, there is provided in an embodiment of the present disclosure

There is provided, in an embodiment of the present disclosure, an imaging method using a radiation source, applied to a treatment device, the treatment device includes the radiation source, and the imaging method includes: emitting, by the radiation source, a beam of rays having a first energy; emitting a beam of rays having a second energy through performing a primary scattering on the beam of rays emitted by the radiation source, the beam of rays applied with the primary scattering passing through a lesion of a human body; wherein the second energy is less than the first energy; receiving the beam of rays passing through the lesion of the human body; and establishing an image of the lesion according to the received beam of rays.

Optionally, the treatment device further comprises a scattering target; and emitting a beam of rays having a second energy through performing a primary scattering on the beam of rays emitted by the radiation source specifically comprises: irradiating the beam of rays having the first energy onto the scattering target, and emitting the beam of rays having the second energy through scattering by the scattering target.

Optionally, before receiving the beam of rays passing through the lesion of the human body, further comprising: filtering the beam of rays to change a spectrum and/or a scattering intensity of the beam of rays.

In another aspect, there is provided a shielding body in an embodiment of the present disclosure, comprising: a radiation source mounting hole, a scattering target area, a scattering channel, and an imaging channel; wherein the radiation source mounting hole is configured to mount a radiation source, and the scattering target area is configured to mount a scattering target; two ends of the scattering channel are respectively in communication with the radiation source mounting hole and the scattering target area; one end of the imaging channel is in communication with the scattering target area; and a beam of rays emitted by the radiation source located at the radiation source mounting hole is irradiated onto the scattering target in the scattering target area through the scattering channel, and is emitted from the imaging channel.

Optionally, the shielding body includes one scattering source mounting hole and at least one scattering channel, and the at least one scattering channel is communicated with the one scattering source mounting hole; or the shielding body comprises a plurality of scattering source mounting holes and a plurality of scattering channels, and at least one of the scattering source mounting holes is in communication with one or more scattering channels; or the shielding body comprises a plurality of scattering channels and one scattering target area, and the plurality of scattering channels are in communication with the scattering target area; or the shielding body comprises a plurality of scattering target areas and at least one imaging channel, and the plurality of the scattering target areas are in communication with the single imaging channel; or the shielding body comprises one scattering target area and a plurality of imaging channels, and the scattering target area is in communication with at least one of the plurality of imaging channels.

Optionally, the shielding body further comprises a scattering switch mechanism, wherein the scattering switch mechanism is configured to open or close a communication state among the radiation source mounting hole, the scattering target area, the scattering channel, and the imaging channel; the scattering switch mechanism is configured to open or close the other end of the imaging channel.

Optionally, an included angle between the scattering channel and the imaging channel is less than 90°.

Optionally, at least two types of paddings are disposed in the imaging channel and average attenuation coefficients of the two types of paddings are different.

Optionally, the average attenuation coefficients of the paddings increase sequentially from the center to the side surface of the imaging channel.

Optionally, the opening of one end of the scattering channel in communication with the scattering target area is smaller than the opening of the other end.

In yet another aspect, there is provided a therapeutic head in an embodiment of the present disclosure, comprising: a radiation source, a scattering target, and the shielding body according to any embodiment of the present disclosure, wherein the radiation source is located at a radiation source mounting hole of the shielding body, and the scattering target is located in a scattering target area of the shielding body.

Optionally, the therapeutic head further comprises a collimator, and the collimator comprises a collimator body, and a plurality of collimating holes and an imaging hole disposed in the collimator body; and a beam of rays emitted by the radiation source is emitted from the collimating holes, and a beam of rays scattered by the scattering target is emitted from the imaging hole.

Optionally, the therapeutic head further comprises a filter layer configured to change a spectrum and/or a scattering intensity of the beam of rays before the beam of rays emitted by the radiation source is irradiated onto a lesion.

Optionally the filter layer is located on the shielding body; or the filter layer is located between the shielding body and the collimator; or the filter layer is located on the collimator.

In still another aspect, there is provided a treatment device in the present disclosure, comprising the therapeutic head according to any embodiment of the present disclosure and a detector; wherein a radiation source of the therapeutic head is capable of emitting a beam of rays; and the detector is configured to receive a beam of rays passing through a lesion of a human body and establish an image of the lesion according to the received beam of rays.

Optionally, the opening of one end of the scattering channel in communication with the scattering target area is smaller than the opening of the other end.

There are provided an imaging method by using a radiation source, a shielding body, a therapeutic head and a treatment device in embodiments of the present disclosure. The imaging method includes: emitting, by the radiation source to emit the beam of rays having a first energy; emitting a beam of rays having a second energy through performing a primary scattering on the beam of rays emitted by the radiation source, the beam of rays applied with the primary scattering passing through the lesion of the human body; wherein the second energy is less than the first energy; receiving the beam of rays passing through the lesion of the human body; and establishing the image of the lesion according to the received beam of rays. The higher the energy of the beam of rays is, the stronger the penetrability is, the intensity attenuation in different substances is not much different, that is, the lesion of the human body is not obviously different from the surrounding tissues thereof, so that the position of the lesion cannot be determined. In the embodiments of the present disclosure, the beam of rays emitted by the radiation source is applied with a primary scattering, to emit the beam of rays having smaller energy used for lesion imaging, such that the lesion and the surrounding tissues thereof can be better distinguished, and a relatively clear image can be formed.

BRIEF DESCRIPTION OF THE DRAWINGS

In order to more clearly explain technical solutions of present disclosure or prior art, the drawings required in description of the embodiments or the prior art will be briefly introduced. It is obvious that the described drawings below are only some embodiments of the present disclosure, and those ordinary skilled in the art can deliver other drawings according to these drawings, without paying any inventive work.

REFERENCE SIGNS

1—radiation source; 2—scattering target; 3—shielding body; 4—collimator; 5—stopper; 10—lesion; 11—therapeutic head; 12—second detector; 21—bulb tube; 22—first detector; 31—radiation source mounting hole; 32—scattering target area; 33—scattering channel; 34—imaging channel; 41—collimator body; 42—collimating hole; 43—imaging hole.

DETAILED DESCRIPTION

The technical solutions in the embodiments of the present disclosure will be described in a clearly and completely way in conjunction with the drawings of the embodiments of the present disclosure. It is obvious that the described embodiments are just a part rather than all of the embodiments of the present disclosure. Based on the embodiments of the present disclosure herein, all the other embodiments derived by those ordinary skilled in the art without any inventive work shall fall within the protection scope of the present disclosure.

Figure 3:
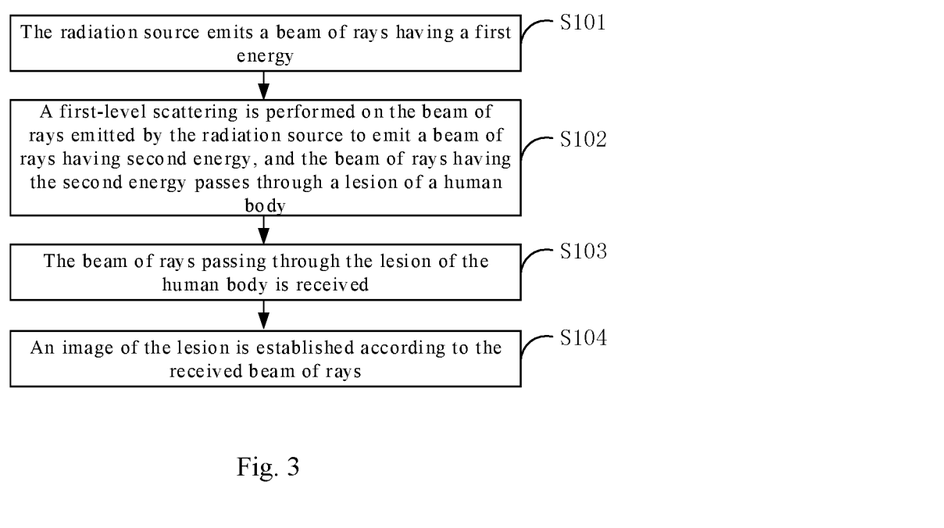
FIG. 3 is a schematic diagram of an imaging method using a radiation source according to an embodiment of the present disclosure.

There is provided an imaging method using a radiation source in an embodiment of the present disclosure. The imaging method is applied to a treatment device. The treatment device includes the radiation source. As shown in FIG. 3, the imaging method includes the following steps.

Step 101, the radiation source emits a beam of rays having a first energy.

Exemplarily, the radiation source may be an X-ray source, an electron source, a nuclide source such as (Co-60), a synchrotron radiation or a neutron source, and the like. The embodiments and the drawings of the present disclosure are all described by taking the nuclear source Co-60 as an example of the radiation source. Herein, the irradiation manner of the radiation source may be focusing or conformed, etc. In the case where the irradiation manner of the radiation source is focusing, there may be a plurality of radiation sources, and the beams of rays emitted by the plurality of radiation sources are focused on a target point. In the case where the irradiation manner of the radiation source is conformed, the beam of rays emitted by the radiation source may be a specific irradiation field formed by a multi-leaf grating or the like.

The radiation source emits the beam of rays having a first energy. The first energy may vary in amount depending on different radiation sources. For example, cobalt-60 (Co-60) is one of the radioisotopes of metallic element cobalt and has a half-life of 5.27 years. In the case where the radiation source is the nuclear source Co-60, the first energy of the beam of rays emitted by the radiation source is 1.33 MeV. For another example, in the case where the radiation source is an x-ray tube, the energy of the X rays emitted by the x-ray tube is adjustable. For example, the first energy of the rays emitted by the x-ray tube may be 200 KV or 150 KV.

Step 102, a primary scattering is performed on the beam of rays emitted by the radiation source to emit a beam of rays having second energy, and the beam of rays applied with the primary scattering passes through a lesion of a human body; wherein the second energy is less than the first energy.

In the embodiments of the present disclosure, a primary scattering performed on the beam of rays emitted by the radiation source may be implemented in various manners, as long as the beam of rays having the second energy can be emitted after the primary scattering, and the second energy is less than the first energy. For example, the beam of rays emitted by the radiation source may be the beam of rays having less energy emitted by the scattering of a shielding body.

Exemplarily, the treatment device further includes a scattering target. The primary scattering is performed on the beam of rays emitted by the radiation source to emit a beam of rays having a second energy specifically includes: the beam of rays having the first energy is irradiated onto the scattering target to cause Compton scattering, and emitting the beam of rays having the second energy through the scattering of the scattering target. Exemplarily, the scattering target may be formed by a substance such as tungsten, iron, lead and carbon, and the energy distribution and intensity of the beam of rays emitted through the scattering of the scattering target formed by different substances are different. The embodiments of the present disclosure do not limit the specific substance composition of the scattering target. Different substances may be selected to form the scattering target according to the amount and intensity requirements on the second energy.

Step 103, the beam of rays passing through the lesion of the human body is received.

In particular, the treatment device may further include a detector. The detector is configured to receive the beam of rays passing through the lesion of the human body. It should be noted that the beam of rays passing through the lesion of the human body is the beam of rays applied with the primary scattering. The higher the energy of the beam of rays for treatment is, the higher the penetrability is, the intensity attenuation in different substances is not much different, that is, the lesion of the human body is not obviously different from the surrounding tissues thereof, so that the position of the lesion cannot be determined. In the embodiments of the present disclosure, a primary scattering is performed on the beam of rays emitted by the radiation source to emit the beam of rays having smaller energy and configured for lesion imaging, such that the lesion and the surrounding tissues thereof can be better distinguished, and a relatively clear image can be formed.

Step 104, an image of the lesion is established according to the received beam of rays.

Exemplarily, the above step 104 specifically includes: projection data of the lesion are acquired according to the received beam of rays, and the image of the lesion is established according to the projection data.

The imaging method by using a radiation source according to the embodiment of the present disclosure is applied to a treatment device. The treatment device includes the radiation source. The imaging method includes: emitting, by the radiation source to emit the beam of rays having a first energy; emitting a beam of rays having a second energy through performing a primary scattering on the beam of rays emitted by the radiation source, the beam of rays applied with the primary scattering passing through the lesion of the human body; wherein the second energy is less than the first energy; receiving the beam of rays passing through the lesion of the human body; and establishing the image of the lesion according to the received beam of rays. The higher the energy of the beam of rays is, the stronger the penetrability is, the intensity attenuation in different substances is not much different, that is, the lesion of the human body is not obviously different from the surrounding tissues thereof, so that the position of the lesion cannot be determined. In the embodiments of the present disclosure, the beam of rays emitted by the radiation source is applied with a primary scattering, to emit the beam of rays having smaller energy used for lesion imaging, such that the lesion and the surrounding tissues thereof can be better distinguished, and a relatively clear image can be formed The embodiment of the present disclosure provides an imaging method, and as shown in FIG. 4, before the step 103, the method further includes the following step.

Step 105, the beam of rays is filtered to change a spectrum and/or a scattering intensity of the beam of rays. Exemplarily, the beam of rays may be filtered by disposing a padding in the imaging channel, which may change a spectrum of the beam of rays only, or change a scattering intensity of the beam of rays only, or change the spectrum and scattering intensity of the beam of rays. Of course, the embodiments of the present disclosure do not specifically limit the manner in which the beam of rays is filtered. For example, the padding may also be disposed in the scattering channel, or the beam of rays is filtered after emitted from the shielding body and before reached the lesion.

Further, at least two types of paddings are disposed in the imaging channel. For example, the average attenuation coefficients of the paddings are gradually increased from the center to the side of the imaging channel, thereby forming the effect that the intensity corresponding to a light field is gradually reduced from the center to the side. The image quality of the acquired projection is enhanced while the imaging dose of the patient is reduced.

Figure 4:
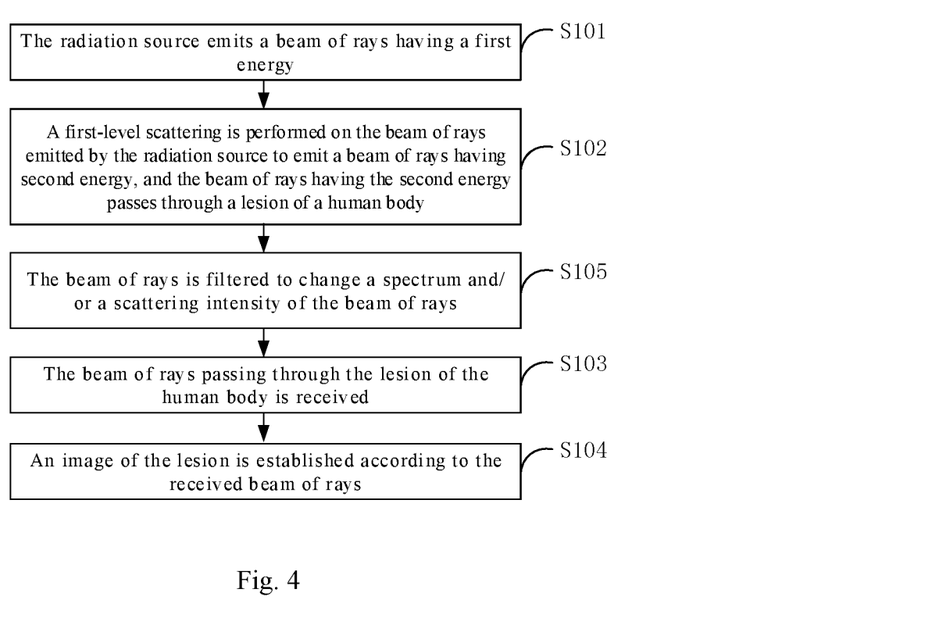
FIG. 4 is a schematic diagram of another imaging method using a radiation source according to an embodiment of the present disclosure.

Of course, the step 105 is not limited to the one shown in FIG. 4. For example, the step 105 may also be performed after the step 101 and before the step 102. The embodiment of the present disclosure takes FIG. 4 as an example for illustration only.

If the beam of rays is filtered, the spectrum of the beam of rays is changed to increase the contrast of the projected image. If the beam of rays is filtered, the scattering intensity of the beam of rays is further reduced, thereby the lesion can be filtered by using the beam of rays having smaller energy. Not only the sharpness of the image can be improved, but also the additional radiation dose received by the patient can be reduced to reduce a secondary damage.

Figure 5:
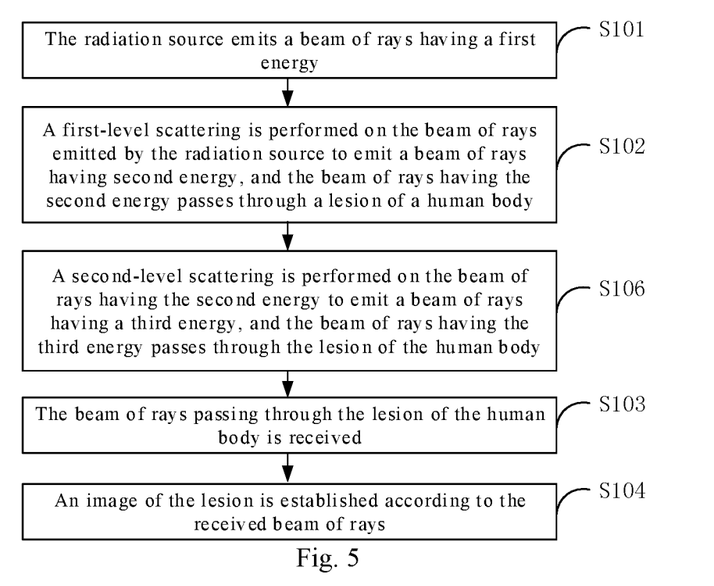
FIG. 5 is a schematic diagram of yet another imaging method using a radiation source according to an embodiment of the present disclosure.

Exemplarily, as shown in FIG. 5, before the beam of rays having the second energy passes through the lesion of the human body, the method further includes the following step.

Step 106, a secondary scattering is performed on the beam of rays having the second energy to emit a beam of rays having a third energy, and the beam of rays applied with the secondary scattering passes through the lesion of the human body. The third second enemy is less than the second energy.

The energy of the beam of rays passing through the lesion of the human body can be further reduced by performing the secondary scattering on the beam of rays having the second energy.

Figure 6:
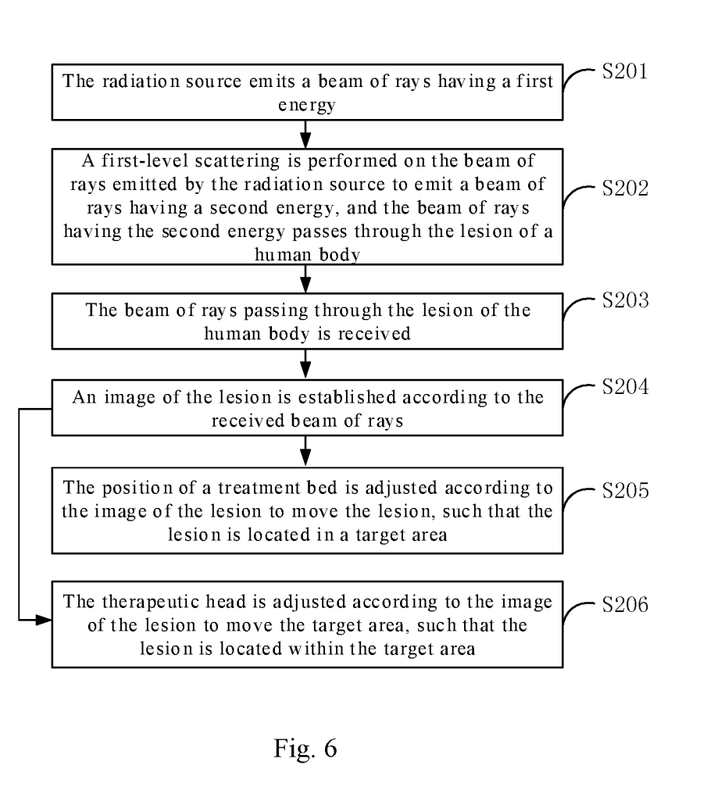
FIG. 6 is a schematic diagram of another method for lesion movement management by using a lesion image of a radiation source according to an embodiment of the present disclosure.

It should be noted that the lesion image formed by using the imaging method according to the embodiments of the present disclosure not only can be used for the pre-treatment positioning, but also can be used for the movement management of the lesion during the treatment. The following is a specific embodiment for illustrating the specific application of the imaging method provided by the embodiment of the present disclosure in the treatment. The present embodiment takes a multi-source focused therapeutic head as an example for illustration, as shown in FIG. 6. Using the lesion image formed by the imaging method according to the embodiment of the present disclosure for the movement management of the lesion during the treatment includes the following steps.

Step 201, the radiation source emits a beam of rays having a first energy.

Step 202, a primary scattering is performed on the beam of rays emitted by the radiation source to emit a beam of rays having a second energy, and the beam of rays applied with the primary scattering passes through the lesion of a human body; wherein the second energy is less than the first energy.

Step 203, the beam of rays passing through the lesion of the human body is received.

Step 204, an image of the lesion is established according to the received beam of rays.

Step 205, the position of a treatment bed is adjusted according to the image of the lesion to move the lesion, such that the lesion is located in a target area.

Generally, the patient lies flat on the treatment bed. The treatment bed may be a three-dimensional bed or a six-position bed, etc., which can be moved up, down, left, and right. Thus, the lesion can be moved by adjusting the position of the treatment bed. Therefore, the lesion is located in the target area to receive a specific dose of the beam radiation from the radiation source in the target area.

Alternatively, the method may further include step 206, the therapeutic head is adjusted according to the image of the lesion to move the target area, such that the lesion is located within the target area.

Generally, the therapeutic head includes the radiation source, a collimator, a shielding body, and the like. By taking multi-source focusing as an example of the radiation source, the beams of rays emitted by the plurality of radiation sources are focused in the target area, such that the position of the target area is adjusted by moving the therapeutic head. Therefore, the lesion is located within the target area to receive a specific dose of the beam radiation from the radiation source in the target area.

According to the imaging method by using a radiation source provided by the embodiment of the present disclosure, the lesion image formed by the imaging method can also be used for movement management the lesion during the treatment process, thereby acquiring the position image of the lesion in real time during the treatment process. The lesion or target area is adjusted according to the position image, so that the lesion receives a specific dose of beam irradiation in the target area, thereby improving the treatment effect. The lesion image formed by the imaging method can also be used for pre-treatment positioning of the patient. Therefore, no imaging system, such as a bulb tube and a corresponding detector, is required, which not only reduces the cost, but also increases the treatment space. The treatment device can not only be used for head treatment, but also can be used for body treatment, thereby achieving the integration of the head treatment and body treatment.

Figure 7:
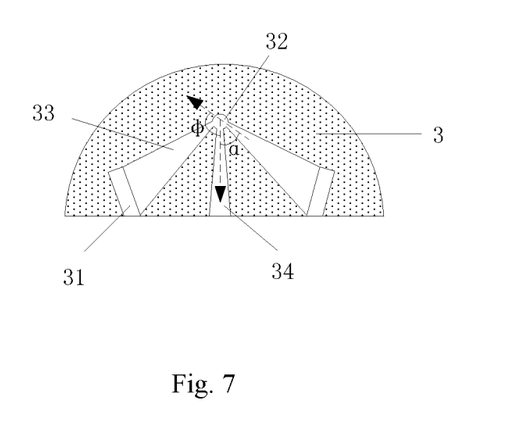
FIG. 7 is a schematic diagram of a shielding body according to an embodiment of the present disclosure.
Figure 8:
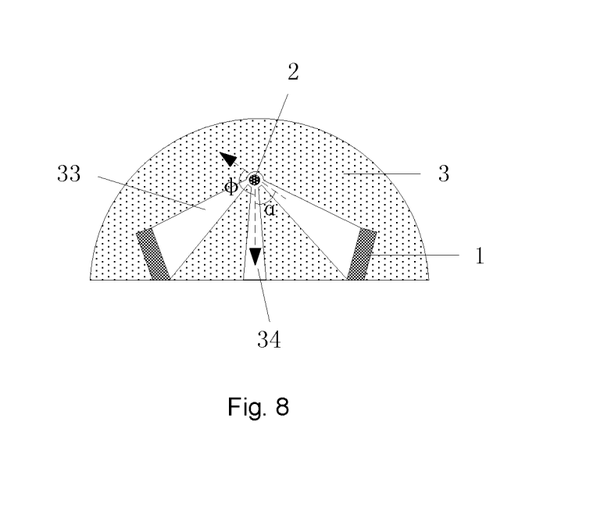
FIG. 8 is a schematic diagram of the shielding body shown in FIG. 7 provided with a radiation source and a scattering target.

As shown in FIG. 7 and FIG. 8, the embodiment of the present disclosure provides a shielding body 3. The shielding body includes a radiation source mounting hole 31, a scattering target area 32, a scattering channel 33, and an imaging channel 34. Herein, the radiation source mounting hole 31 is configured to mount a radiation source 1. The scattering target area 32 is configured to mount a scattering target 2. Both ends of the scattering channel 33 are in communication with the radiation source mounting hole 31 and the scattering target area 32 respectively. One end of the imaging channel 34 is in communication with the scattering target area 33. The beam of rays emitted by the radiation source 1 located at the radiation source mounting hole 31 is irradiated onto the scattering target 2 in the scattering target area 32 by the scattering channel 33, and is emitted from the imaging channel 33.

It should be noted that FIG. 7 and FIG. 8 are exemplified by including two radiation sources. The embodiments of the present disclosure do not specifically limit the position, layout, structure, and the like of the radiation source, the imaging channel, the scattering channel, and the like. In addition, the number of the radiation source is not limited either. For example, the radiation source may be a single source or multiple sources. The shielding body can shield the radiation source, and is generally formed by the material with a better shielding effect, such as lead. In the embodiments of the present disclosure, exemplarily, the attenuation coefficient of the scattering target for the beam of rays is smaller than the attenuation coefficient of the shielding beam for the beam of rays, thereby ensuring that energy of the beam of rays after the scattering of the scattering target is not too small for irradiation imaging of the lesion.

The shielding body provided in the embodiments of the present disclosure includes the radiation source mounting hole, the scattering target area, the scattering channel and the imaging channel. The radiation source mounting hole is configured to mount the radiation source. The scattering target area is configured to mount the scattering target. The attenuation coefficient of the scattering target for the beam of rays is smaller than the attenuation coefficient of the shielding body for the beam of rays. Both ends of the scattering channel are respectively in communication with the radiation source mounting hole and the scattering target area. One end of the imaging channel is in communication with the scattering target area. The beam of rays emitted by the radiation source located at the radiation source mounting hole is irradiated onto the scattering target in the scattering target area by the scattering channel. The beam of rays scattered by the scattering target is then emitted from the imaging channel. The energy of the beam of rays scattered by the scattering target is lower than the energy of the beam of rays emitted by the radiation source. Therefore, the scattered beam of rays is used for passing through the lesion of the patient for imaging, the radiation dose received by the patient is low, and the contrast of the formed image is high. The lesion of the patient can be more clearly displayed.

The shielding body provided by the embodiments of the disclosure includes one scattering source mounting hole and at least one scattering channel. The at least one scattering channel is in communication with the scattering source mounting hole. The radiation source disposed at the scattering source mounting hole emits to the scattering target through the plurality of scattering channels. Therefore, the energy reaching the scattering target can be adjusted via the number of the scattering channels to further adjust the energy of the beam of rays for imaging.

Exemplarily, the shielding body includes one scattering source mounting hole, that is, the treatment device including the shielding body includes one radiation source. By taking cobalt-60 as an example of the radiation source, the treatment device including the shielding body may further include a collimator and a multi-leaf grating. The radioactive rays emitted by the radiation source are emitted from the collimator, which converts the radiation source into a point source. The multi-leaf grating can be conformed according to the shape of a tumor, thereby achieving conformed intensity-modulated radiation therapy.

The shielding body provided by the embodiments of the present disclosure includes a plurality of scattering source mounting holes and a plurality of scattering channels. The at least one scattering source mounting hole is in communication with one or more scattering channels. For example, the shielding body includes ten scattering source mounting holes, only one scattering source mounting hole may be in communication with the scattering channel, the communication between the plurality of scattering source mounting holes and the scattering target is avoided, and the problem that the beam of rays scattered by the scattering target still has a larger dose is caused. Of course, the one scattering source mounting hole may be in communication with one scattering channel or a plurality of scattering channels, so as to further adjust the energy of the beam of rays at the scattering target.

The shielding body provided by the embodiments of the present disclosure includes a plurality of scattering channels and one scattering target area. The plurality of scattering channels is in communication with the scattering target area. Exemplarily, as shown in FIG. 7 and FIG. 8, by taking two scattering source mounting holes as an example, the two scattering source mounting holes are respectively in communication with one scattering channel, and the two scattering channels are in communication with one scattering target. Therefore, the scattering target located in the scattering target area receives the beams of rays of different scattering channels.

The shielding body provided by the embodiments of the present disclosure includes a plurality of scattering target areas and at least one imaging channel. The plurality of scattering target areas is in communication with the same imaging channel. For example, if the scattering target of the scattering target area is lead, the energy of the beam of rays after the scattering of the scattering target is very small. Therefore, the beams of rays scattered by the plurality of scattering targets can be emitted by the same imaging channel, so as to increase the energy of the scattered beams of rays.

The shielding body provided by the embodiments of the present disclosure includes one scattering target area and a plurality of imaging channels. The scattering target area is in communication with at least one of the plurality of imaging channels. The beams of rays emitted by the plurality of imaging channels may be intersected in the target area, such that the beams of rays of respective imaging channels can be sequentially received by controlling the detector. Therefore, a three-dimensional image for the lesion can be formed.

It should be noted that the energy of the radiation source differs according to the type of the radiation source. For example, the energies corresponding to the cobalt sources having different activities are different. The energies of X rays emitted by the X-ray source according to different voltages or currents are also different. The present disclosure does not limit the energy of the radiation source, and different shielding bodies can be used according to the radiation resources having different energies to realize three-dimensional imaging.

The embodiment of the present disclosure provides a shielding body, and the shielding body further includes a scattering switch mechanism. The scattering switch mechanism is configured to open or close the communication state between the radiation source mounting hole, the scattering target area, the scattering channel and the imaging channel. Alternatively, the scattering switch mechanism is configured to open or close the other end of the imaging channel.

Specifically, both ends of the scattering channel are respectively in communication with the radiation source mounting hole and the scattering target area, and one end of the imaging channel is in communication with the scattering target area. Then the radiation source mounting hole, the scattering channel, the scattering target area, and the imaging channel are in the communication state. The scattering switch mechanism is configured to open or close the communication state between the radiation source mounting hole, the scattering target area, the scattering channel, and the imaging channel. That is, the communication state between the radiation source mounting hole and the scattering target area can be opened or closed, or the communication state between the scattering target area and the scattering channel can be opened or closed, or the communication state between the scattering channel and the imaging channel can be opened or closed, which is not specifically limited by the embodiments of the present disclosure.

Of course, the scattering switch mechanism is configured to open or close the other end of the imaging channel, that is, to open or close the imaging channel, so that the radioactive rays are emitted or shielded.

Exemplarily, the scattering switch mechanism may form closing by misalignment, or by using other stoppers. The specific implementation manner of the scattering switch mechanism is not limited by the embodiments of the present disclosure.

The energy and intensity of the scattered rays are related to an included angle α between the imaging channel and a beam channel in addition to the energy from the initial rays of the radiation source (i.e., the first energy in the embodiments of the present disclosure). In the embodiments of the present disclosure, the included angle α between the imaging channel and the beam channel is not limited. But preferably, as shown in FIG. 7 and FIG. 8, the included angle α between the scattering channel 33 and the imaging channel 34 is less than 90°. According to the principle of Compton scattering, the variation of the wavelength after scattering increases as the increasing of the included angle between a scattering direction and an incident direction and the increasing of the included angle φ shown in FIG. 7 and FIG. 8. That is, the larger the included angle between the scattering direction and the incident direction is, the larger the wavelength of the scattered beam is and the smaller the energy is. Referring to FIG. 7 and FIG. 8, in the embodiments, relative to α>90°, in the case that α<90°, the scattered photon energy is lower, the imaging quality is higher, and the imaging dose received by the patient is also lower.

According to the shielding body provided by the embodiments of the present disclosure, the opening of one end of the imaging channel in communication with the scattering target area is smaller than the opening of the other end. As shown in FIG. 7 and FIG. 8, the opening of the imaging channel is a tapered opening, so that the scattered rays emitted by the scattering target are an outwardly diverging beam of rays.

Further, the opening of one end of the scattering channel in communication with the scattering target area is smaller than the opening of the other end.

Figure 9:
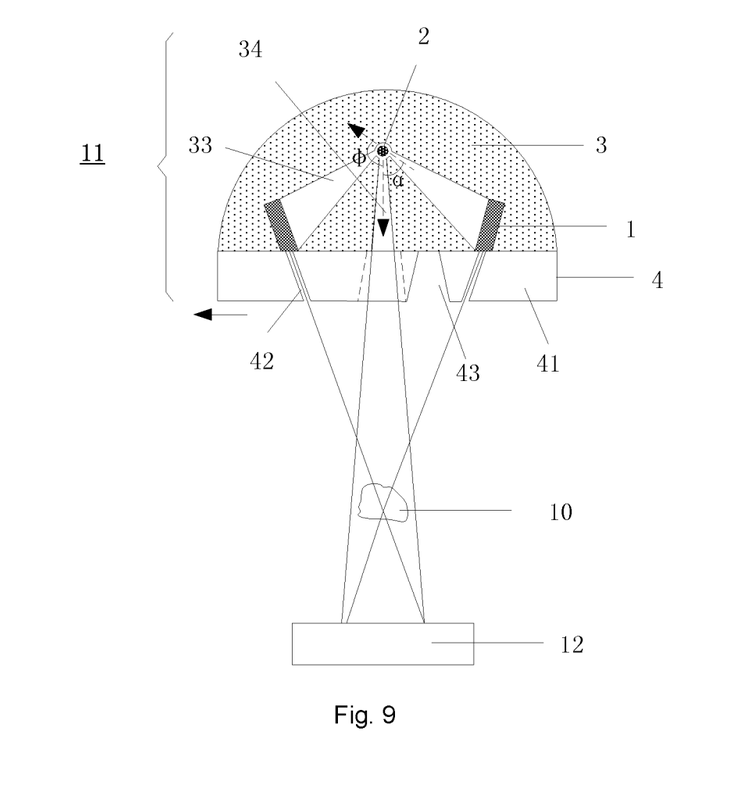
FIG. 9 is a schematic diagram of lesion imaging by a therapeutic head according to an embodiment of the present disclosure.

An embodiment of the present disclosure provides a therapeutic head 11, as shown in FIG. 9, which includes: a radiation source 1, a scattering target 2, and any one shielding body 3 according to embodiments of the present disclosure. The radiation source 1 is located in a radiation source mounting hole of the shielding body 3. The scattering target 2 is located in a scattering target area of the shielding body.

The therapeutic head according to the embodiments of the present disclosure, as shown in FIG. 9, further includes a collimator 4. The collimator 4 includes a collimator body 41, and a plurality of collimating holes 42 and an imaging hole 43 disposed in the collimator body 41. The beam of rays emitted by the radiation source 1 is emitted from the collimating holes 42 for treatment of the patient. The collimator 4 is moved along the arrow as shown in FIG. 9, such that the beam of rays scattered by the scattering target 2 is emitted from the imaging hole 42, so as to image the lesion with the radiation scattered by the scattering target.

In the therapeutic head shown in FIG. 9, the imaging hole 43 in the collimator 4 is staggered from the imaging channel 34, so that by moving the collimator 4, the imaging hole 43 can be aligned with the imaging channel 34, thereby enabling the beam of rays scattered by the scattering target 2 to be emitted from the imaging hole 42. It is equivalent to opening or closing of the imaging channel 34 by the movement of the collimator 4, so that the beam of rays scattered by the scattering target 2 is used for imaging of the lesion 10 or is shielded by the collimator 4. Of course, the manner whether the beam of rays scattered by the scattering target is used for imaging is varied, and is not limited to that shown in FIG. 9. Exemplarily, in the case where the shielding body further includes the scattering switch mechanism, the imaging hole may also be directly aligned with the opening of the imaging channel.

Figure 10:
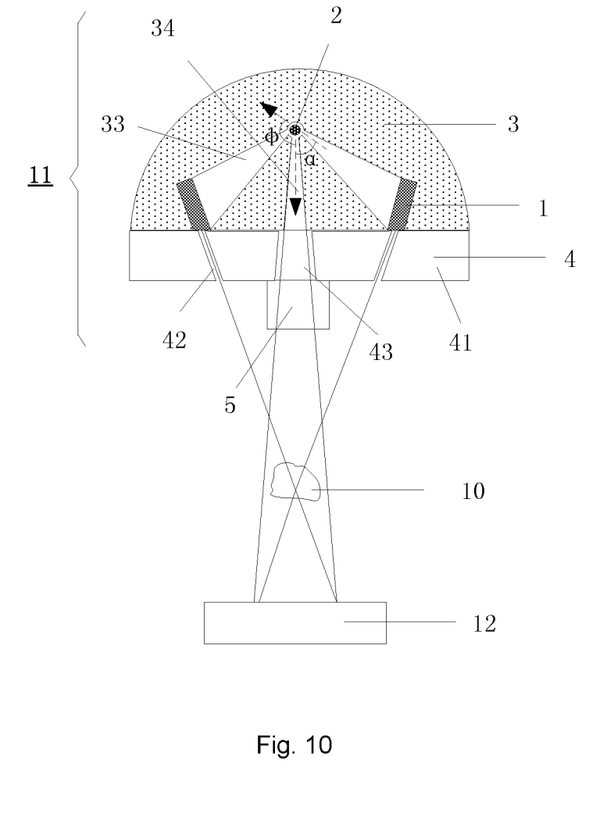
FIG. 10 is another schematic diagram of lesion imaging by the therapeutic head according to an embodiment of the present disclosure.

FIG. 10 shows another manner for controlling the beam of rays scattered by the scattering target for imaging or not provided by the embodiments of the present disclosure. The therapeutic head 11 further includes a stopper 5, and the imaging hole 43 is aligned with the imaging channel 34. Therefore, the beam of rays scattered by the scattering target 2 is used for imaging of the lesion 10 by moving the stopper 5 or is shielded by the stopper 5.

The therapeutic head provided in the embodiment of the present disclosure further includes a filter layer, configured to change a spectrum and/or a scattering intensity of the beam of rays emitted by the radiation source before the beam of rays is irradiated onto the lesion.

Exemplarily, the filter layer may be located on the shielding body; or the filter layer may be located between the shielding body and the collimator; or the filter layer may be located on the collimator.

An embodiment of the present disclosure provides a treatment device, including any one of therapeutic heads provided by the embodiments of the present disclosure and a detector. The radiation source of the therapeutic head emits a beam of rays. The detector is configured to receive the beam of rays passing through the lesion of a human body, and establish an image of the lesion according to the received beam of rays.

It should be noted that the detector generally includes a detector plate. The detector plate generally includes a plurality of small pixel plates arranged in array. Each pixel plate may receive the beam of rays. The detector performs data processing on the beam of rays received by each pixel plate, to establish the image of the lesion.

The above description is merely specific embodiments of the present disclosure, and the protection scope of the present disclosure is not limited thereto. The variations or modifications easily conceived by a person skilled in the art shall be encompassed within the protection scope of the present disclosure. Therefore, the protection scope of the present disclosure shall be defined by the appended claims.

What is claimed is:

1. An imaging method using a radiation source, applied to a treatment device, the treatment device comprises the radiation source, and the imaging method comprises:
    emitting, by the radiation source, a beam of rays having a first energy;
    emitting a beam of rays having a second energy by performing a primary scattering on the beam of rays emitted by the radiation source, the beam of rays applied with the primary scattering passing through a lesion of a human body; wherein the second energy is less than the first energy;
    receiving the beam of rays passing through the lesion of the human body; and
    establishing an image of the lesion according to the received beam of rays.

2. The imaging method according to claim 1, wherein:
    the treatment device further comprises a scattering target; and
    emitting the beam of rays having the second energy through performing the primary scattering on the beam of rays emitted by the radiation source comprises:
    irradiating the beam of rays having the first energy onto the scattering target, and emitting the beam of rays having the second energy through scattering by the scattering target.

3. The imaging method according to claim 1, before receiving the beam of rays passing through the lesion of the human body, further comprising:
   filtering the beam of rays to change at least one of a spectrum and a scattering intensity of the beam of rays.

4. A shielding body, comprising:
   a radiation source mounting hole, a scattering target area, a scattering channel, and an imaging channel, wherein the radiation source mounting hole is configured to mount a radiation source, and the scattering target area is configured to mount a scattering target;
   two ends of the scattering channel are respectively in communication with the radiation source mounting hole and the scattering target area;
   one end of the imaging channel is in communication with the scattering target area; and
   a beam of rays emitted by the radiation source located at the radiation source mounting hole is irradiated onto the scattering target in the scattering target area through the scattering channel, and is emitted from the imaging channel.

5. The shielding body according to claim 4, wherein the shielding body comprises one scattering source mounting hole and at least one scattering channel, and the at least one of scattering channels is in communication with the one scattering source mounting hole.

6. The shielding body according to claim 4, wherein the shielding body further comprises a scattering switch mechanism, wherein the scattering switch mechanism is configured to open or close a communication state among the radiation source mounting hole, the scattering target area, the scattering channel, and the imaging channel.

7. The shielding body according to claim 4, wherein an included angle between the scattering channel and the imaging channel is less than 90°.

8. The shielding body according to claim 4, wherein at least two types of paddings are disposed in the imaging channel and average attenuation coefficients of the two types of paddings are different.

9. The shielding body according to claim 4, wherein the shielding body comprises a plurality of scattering source mounting holes and a plurality of scattering channels, and at least one of the plurality of scattering source mounting holes is in communication with at least one of the plurality of scattering channels.

10. The shielding body according to claim 4, wherein the shielding body comprises a plurality of scattering channels and one scattering target area, and the plurality of scattering channels are in communication with the one scattering target area.

11. The shielding body according to claim 4, wherein the shielding body comprises a plurality of scattering target areas and at least one imaging channel, and the plurality of the scattering target areas are in communication with the same imaging channel.

12. The shielding body according to claim 4, wherein the shielding body comprises one scattering target area and a plurality of imaging channels, and the one scattering target area is in communication with at least one of the plurality of imaging channels.

13. The shielding body according to claim 4, wherein the shielding body further comprises a scattering switch mechanism, wherein the scattering switch mechanism is configured to open or close the other end of the imaging channel.

14. A therapeutic head, comprising:
   a radiation source;
   a scattering target;
   the shielding body comprising: a radiation source mounting hole, a scattering target area, a scattering channel, and an imaging channel,
   wherein the radiation source mounting hole is configured to mount the radiation source, and the scattering target area is configured to mount the scattering target;
   two ends of the scattering channel are respectively in communication with the radiation source mounting hole and the scattering target area;
   one end of the imaging channel is in communication with the scattering target area; and
   a beam of rays emitted by the radiation source located at the radiation source mounting hole is irradiated onto the scattering target in the scattering target area through the scattering channel, and is emitted from the imaging channel, wherein the radiation source is located at the radiation source mounting hole of the shielding body, and the scattering target is located in the scattering target area of the shielding body.

15. The therapeutic head according to claim 14, wherein:
   the therapeutic head further comprises a collimator, and the collimator comprises a collimator body, and a plurality of collimating holes and an imaging hole in the collimator body; and
   the beam of rays emitted by the radiation source is emitted from the collimating holes, and the beam of rays scattered by the scattering target is emitted from the imaging hole.

16. The therapeutic head according to claim 14, wherein the therapeutic head further comprises a filter layer configured to change at least one of a spectrum and a scattering intensity of the beam of rays before the beam of rays emitted by the radiation source is irradiated onto a lesion.

17. The therapeutic head according to claim 16, wherein the filter layer is at one of the following: on the shielding body, between the shielding body and the collimator, and on the collimator.

18. The shielding body according to claim 14, wherein the average attenuation coefficients of the paddings increase sequentially from a center to a side surface of the imaging channel.

19. A treatment device, comprising:
   a therapeutic head comprising a radiation source, a scattering target, and a shielding body comprising: a radiation source mounting hole, a scattering target area, a scattering channel, and an imaging channel;
   wherein the radiation source mounting hole is configured to mount the radiation source, and the scattering target area is configured to mount the scattering target;
   two ends of the scattering channel are respectively in communication with the radiation source mounting hole and the scattering target area;
   one end of the imaging channel is in communication with the scattering target area;
   a detector;
   wherein the radiation source of the therapeutic head located at the radiation source mounting hole is capable of emitting a beam of rays irradiated onto the scattering target in the scattering target area through the scattering channel, and is emitted from the imaging channel, wherein the radiation source is located at a radiation source mounting hole of the shielding body, and the scattering target is located in a scattering target area of the shielding body; and the detector is configured to receive the beam of rays passing through a lesion of a human body and establish an image of the lesion according to the received beam of rays.

20. The treatment device according to claim 19, wherein:

the therapeutic head further comprises a collimator, and the collimator comprises a collimator body, and a plurality of collimating holes and an imaging hole disposed in the collimator body; and a beam of rays emitted by the radiation source is emitted from the collimating holes, and a beam of rays scattered by the scattering target is emitted from the imaging hole.

\* \* \* \* \*